(12) United States Patent　　　　(10) Patent No.:　US 12,691,196 B2

Thompson　　　　　　　　　　　　　(45) Date of Patent:　　　Jul. 28, 2026

(54) AIR FRESHENER HOLDER

(71) Applicant: James Thompson, Greenacres, WA (US)

(72) Inventor: James Thompson, Greenacres, WA (US)

( * ) Notice: Subject to any disclaimer, the term of this patent is extended or adjusted under 35 U.S.C. 154(b) by 121 days.

(21) Appl. No.: 18/658,954

(22) Filed: May 8, 2024

(65) Prior Publication Data

US 2024/0374775 A1　　Nov. 14, 2024

Related U.S. Application Data

(60) Provisional application No. 63/500,832, filed on May 8, 2023.

(51) Int. Cl.
　　*A61L 9/00*　　　　　(2006.01)
　　*A61L 9/12*　　　　　(2006.01)

(52) U.S. Cl.
　　CPC ........... *A61L 9/12* (2013.01); *A61L 2209/133* (2013.01); *A61L 2209/15* (2013.01)

(58) Field of Classification Search
　　USPC ........................................................ 239/57
　　See application file for complete search history.

(56)　　　　　　　References Cited

U.S. PATENT DOCUMENTS

| | | | |
|---|---|---|---|
| 5,651,522 A | 7/1997 | Davis et al. | |
| 5,868,315 A * | 2/1999 | Chen ......................... | A61L 9/12 |
| | | | 239/57 |
| 9,278,152 B2 | 3/2016 | Irwin et al. | |
| 9,642,928 B1 | 5/2017 | Rapoza | |
| 10,933,721 B2 | 3/2021 | Pirovolikos et al. | |
| 2004/0169091 A1* | 9/2004 | Wheatley ................ | A61L 9/048 |
| | | | 239/57 |
| 2015/0306268 A1* | 10/2015 | Torres ....................... | A61L 9/04 |
| | | | 239/57 |
| 2016/0310626 A1 | 10/2016 | Duca et al. | |

* cited by examiner

*Primary Examiner* — Edwin Kang

(74) *Attorney, Agent, or Firm* — KNH LLP

(57)　　　　　　　ABSTRACT

Apparatuses, systems, and methods are disclosed for an air freshener holder. An apparatus includes a body that includes a slot configured to receive an air freshener, a front side that includes at least one opening, and a back side that includes attachment means for coupling the body to a surface.

16 Claims, 8 Drawing Sheets

100

112

110

114 118

104 116

102

108

106

112

100

110

112

122

120

114

118

116

102

106

200

202 providing an air freshener

204 providing a body that includes a slot configured to receive an air freshener, a front side that includes at least one opening, and a back side that includes attachment means for coupling the body to a surface

AIR FRESHENER HOLDER

CROSS-REFERENCE TO RELATED APPLICATIONS

This application claims the benefit of U.S. Provisional Patent Application No. 63/500,832 entitled "AIR FRESH-ENER HOLDER" and filed on May 8, 2023, for James Thompson, which is incorporated herein by reference.

FIELD

The subject matter disclosed herein relates to air fresheners and more particularly relates to a holder for an air freshener.

BACKGROUND

In general, air fresheners typically emit fragrance and are used in homes or commercial interiors such as restrooms, foyers, hallways, vestibules, and other smaller indoor areas, as well as larger areas such as hotel lobbies, auto dealer-ships, medical facilities, public arenas and other large interior spaces. Car fresheners are used in automobiles.

SUMMARY

Apparatuses, systems, and methods are disclosed for an air freshener holder. In one embodiment, an apparatus includes a body that includes a slot configured to receive an air freshener, a front side that includes at least one opening, and a back side that includes attachment means for coupling the body to a surface.

In one embodiment, a system includes an air freshener and a body that includes a slot configured to receive an air freshener, a front side that includes at least one opening, and a back side that includes attachment means for coupling the body to a surface.

In one embodiment, a method includes providing an air freshener and providing a body that includes a slot config-ured to receive an air freshener, a front side that includes at least one opening, and a back side that includes attachment means for coupling the body to a surface.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

In general, the subject matter disclosed herein relates to an air freshener holder. In particular, the air freshener holder is configured to be secured to a surface to emit a scent provided by an air freshener that is placed within the air freshener holder. Further, the air freshener holder may include an external holder for a separate air freshener. In this manner, the proposed solutions provide means for providing a holder for air fresheners that can be placed on a surface that may not otherwise have a place for mounting an air freshener.

Figure 1A:
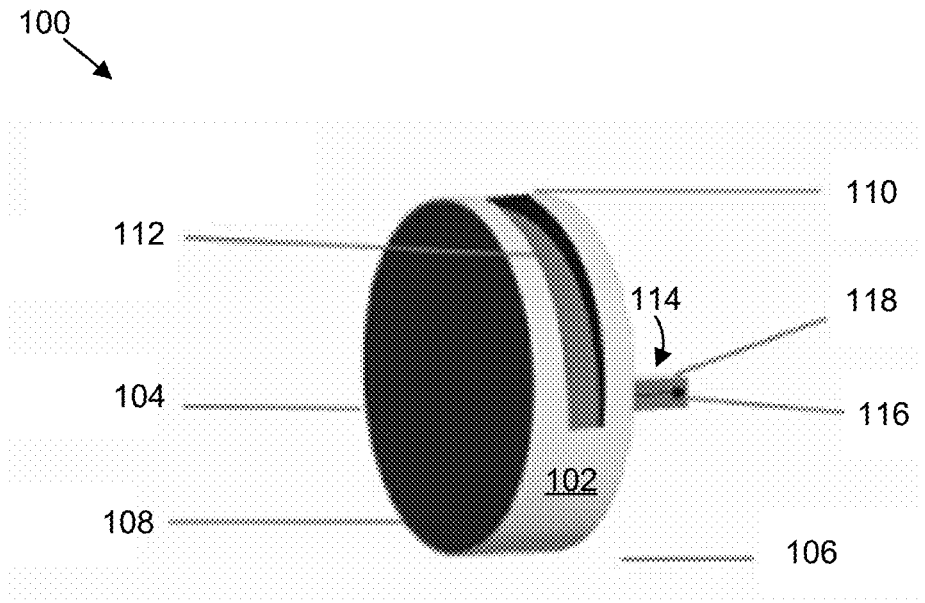
FIG. 1A illustrates an example embodiment of an air freshener holder in accordance with the subject matter disclosed herein.

FIG. 1A illustrates an example embodiment of an air freshener holder 100. In one embodiment, the air freshener holder 100 comprises a body 102. The body 102 may be made of a substantially rigid material such as plastic, metal, or the like. For instance, in one embodiment, the body 102 is thermoformed using a plastic material. In one embodi-ment, the body 102 has a substantially round or cylindrical shape, as shown in FIG. 1A. In various embodiments, however, the body 102 may take several different shapes such as square/cubic, triangular/pyramid, and/or the like.

In one embodiment, the body 102 includes a back side 104 and a front side 106. The back side 104, in one embodiment, may include attachment means such as an adhesive 108 or other material, for coupling the air freshener holder 100 to a surface, e.g., a dashboard, a wall, glass, or the like. In one embodiment, the attachment means may include an adhesive, sticky material, glue, tape, magnets, a suction cup, and/or the like.

In one embodiment, the back side 104 may be shaped to conform to a particular surface. For example, the back side 104 of the body 102 may have a concave shape to match a corresponding convex shape of a surface where the air freshener holder 100 is installed. In some embodiments, the back side 104 is flexible to conform to surfaces with different contours.

Figure 1B:
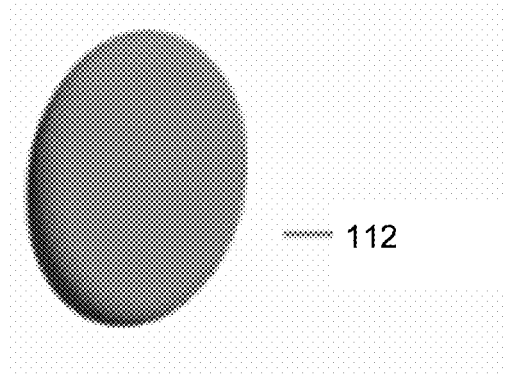
FIG. 1B illustrates an example embodiment of an air freshener holder in accordance with the subject matter disclosed herein.

In one embodiment, the body 102 includes a slot 110 or other opening for inserting an air freshener 112. As shown in FIG. 1B, the air freshener 112 may have a shape that matches the shape of the air freshener holder 100, e.g., a disc. The air freshener 112 may be made of a substantially rigid material such as plastic, cardstock, cardboard, or the like where the material is able to absorb air freshener material and emit scents from the air freshener holder 100.

Referring again to FIG. 1A, the air freshener holder 100 further includes an external holder 114 on the front side 106 for a separate air freshener with a string-type holder. In one embodiment, the external holder 114 includes a slot 116, groove, channel, or the like for holding a string or other attachment member of a separate air freshener. In further embodiments, the external holder 114 includes a lever mechanism 118 that opens to allow the string or other attachment member of the separate air freshener to be placed into the slot 116 and closes to secure the string or other attachment member of the separate air freshener within the slot 116. In such an embodiment, the lever mechanism 118 is secured or locked in a closed position using magnets, clips, snaps, or other securing means. In one embodiment, the external holder 114 is coupled to the body 102 using a hinge such that the external holder 114 can be folded into the body 102 so that it is flush with a surface of the front side 106.

Figure 1C:
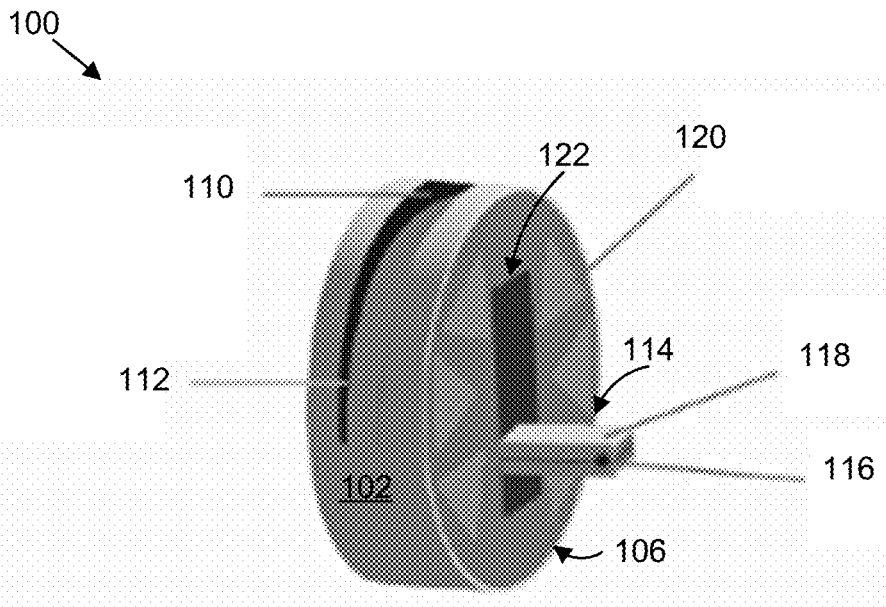
FIG. 1C illustrates an example embodiment of an air freshener holder in accordance with the subject matter disclosed herein.

FIG. 1C illustrates an example embodiment of an air freshener holder 100. In one embodiment, the front 106 of the body 102 of the air freshener holder 100 includes one or more openings 120, vents, windows, or the like for allowing the scent of the air freshener 112 within the body 102 to be emitted. The body 102 may include multiple openings, may include a single opening (e.g., a ring-shaped opening), or the like.

In the embodiment shown in FIG. 1C, the external holder 114 may be rotatably connected to the front side 106 of the body 102, e.g., via a hinge, so that it can be pushed and rotated into a recess 122 within the front side 106 of the body 102 such that it sits flush with the surface of the front side 106 of the body 102, e.g., so that it does not protrude out from the surface of the front side 106 of the body 102. In such an embodiment, when the external holder 114 is depressed within the recess 122 within the front 106 of the body 102, the external holder 114 may be secured within the recess 122 using securing means such as a magnet, a snap fit, a friction fit, or the like. For example, the securing means may include a push lock mechanism such that when the external holder 114 is pushed into the recess 122, it is locked in place and may be disengaged and released when the external holder 114 is pushed again.

Figure 1D:
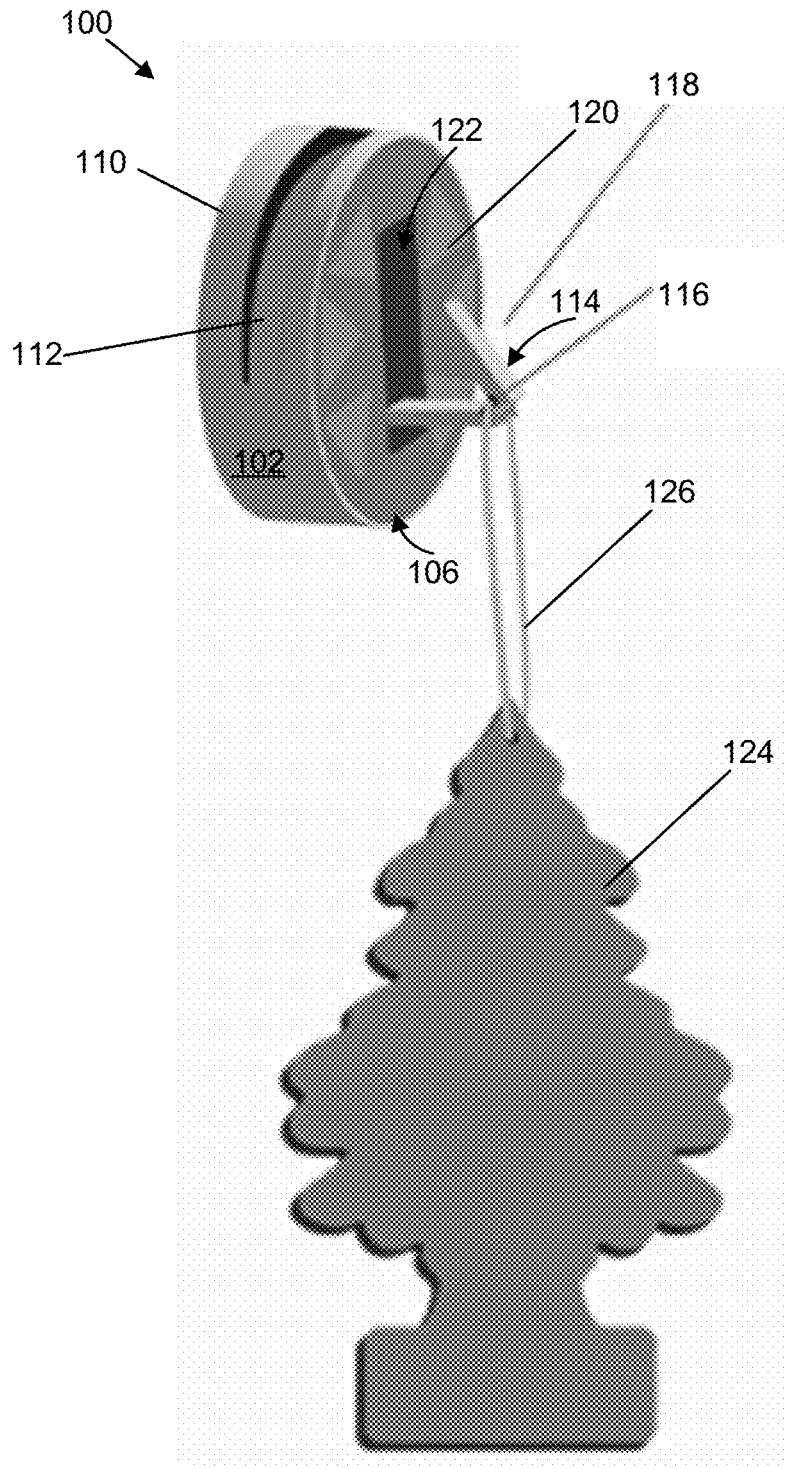
FIG. 1D illustrates an example embodiment of an air freshener holder in accordance with the subject matter disclosed herein.

FIG. 1D illustrates an example embodiment of an air freshener holder 100. In particular, FIG. 1D illustrates use of the external holder 114 for a separate air freshener 124. The separate air freshener 124 may have a string 126 that is used to hang the separate air freshener 124. In one embodiment, the external holder 114 is released from the recess 122 and the lever 118 is opened to insert the string 126 into the slot 116. In one embodiment, the lever 118 is closed, to secure the string 126 within the slot 116, and the external holder 114 may be depressed into the recess 122.

Figure 1E:
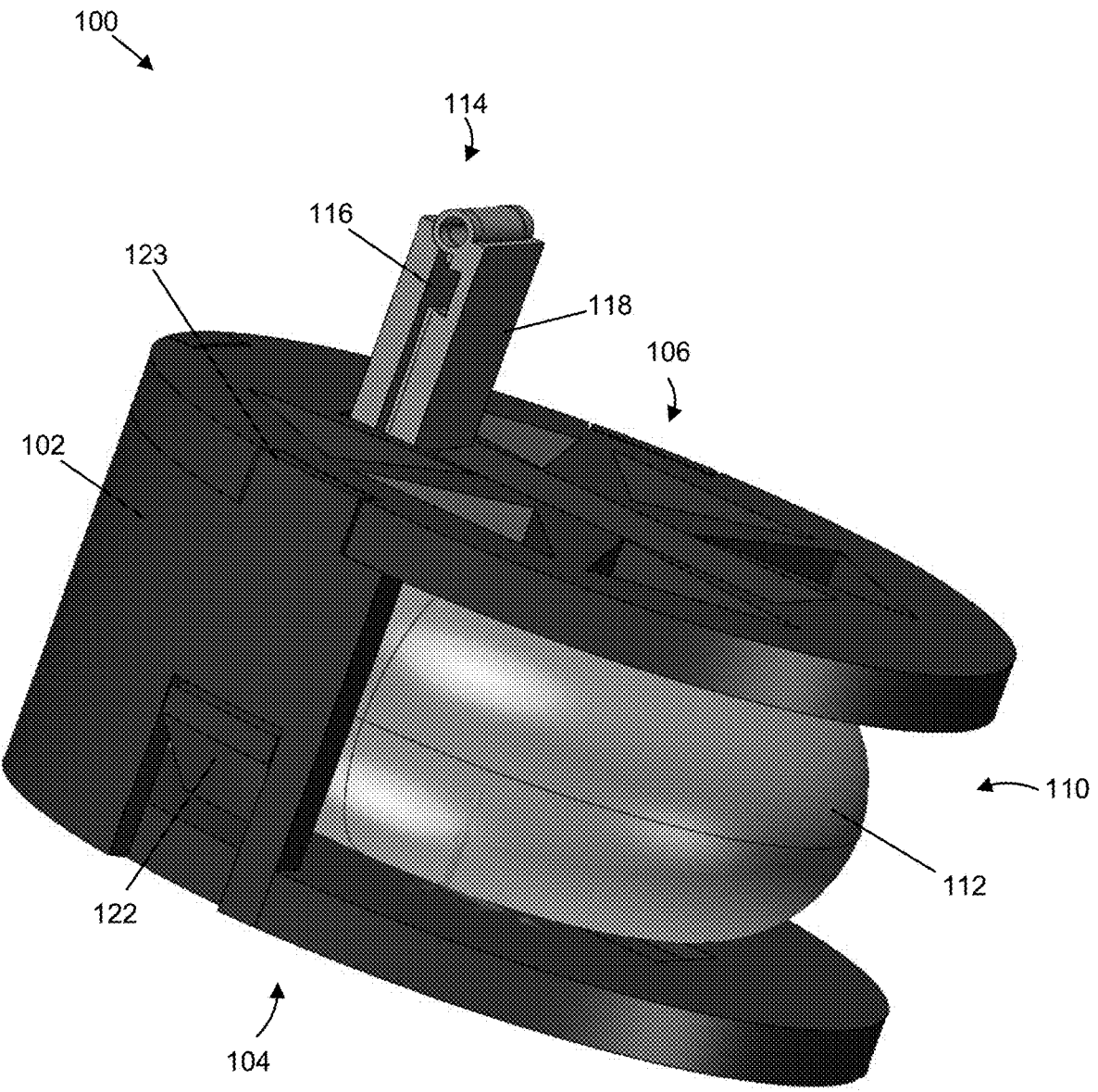
FIG. 1E illustrates another example embodiment of an air freshener holder in accordance with the subject matter disclosed herein.

FIG. 1E illustrates another example embodiment of an air freshener holder 100. In one embodiment, the front side 106 is coupled to the back side 104 using a series of clips 122 and protrusions 123 that correspond to openings and grooves in the opposite side.

Figure 1F:
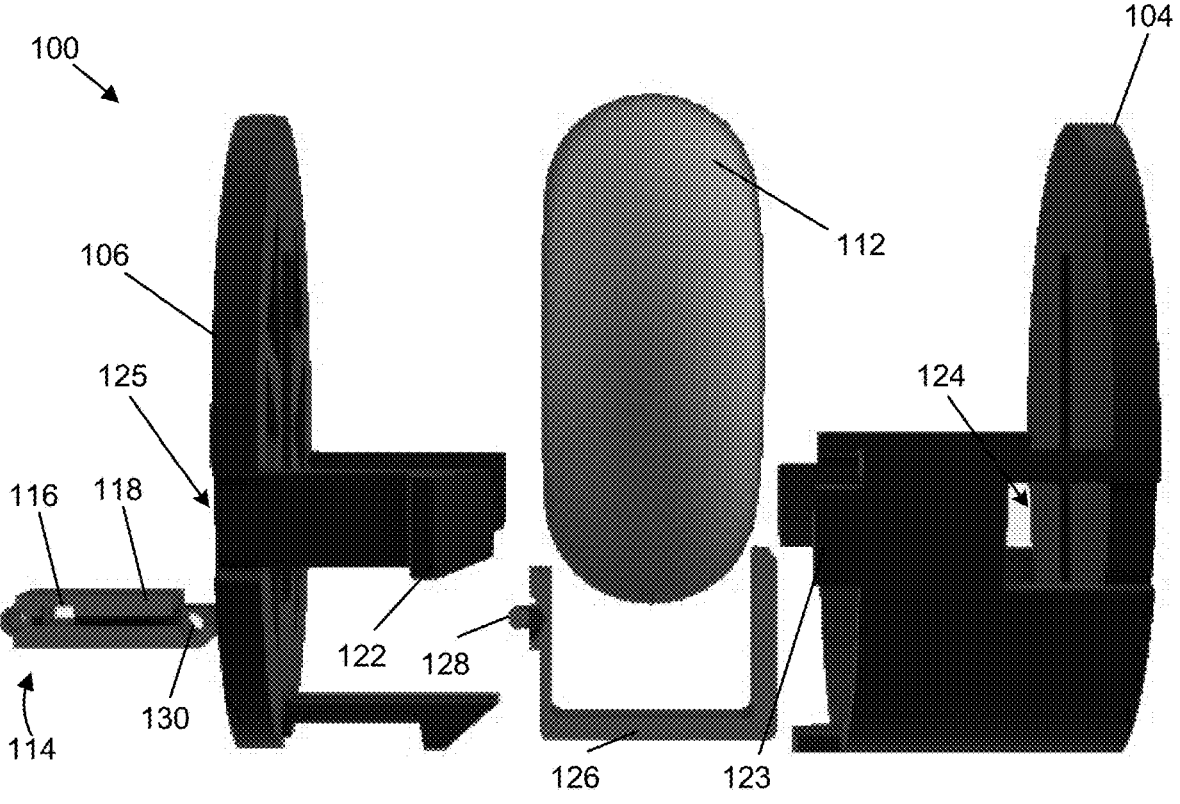
FIG. 1F illustrates an exploded view of an embodiment of an air freshener holder in accordance with the subject matter disclosed herein.

FIG. 1F illustrates an exploded view of an embodiment of an air freshener holder 100. In the depicted embodiment, the front side 106 is coupled with the back side 104 by inserting clips 122 on the front side 106 into corresponding openings 124 in the back side 104. Further, protrusions 123 on the back side 104 are inserted into corresponding grooves 125 on the front side 106 to help secure the front side 106 to the back side 104.

In one embodiment, the air freshener holder 100 includes a base member 126 that holds the air freshener 112 in place. The base member 126 may further include a pin 128 that is inserted into a corresponding opening 130 in the lever mechanism 114 to secure the lever mechanism to the air freshener holder 100 and allow the lever mechanism to collapse or retract into the front side 106 and be expand outward from the front side 106 to secure a different air freshener within the lever mechanism 114.

Figure 1G:
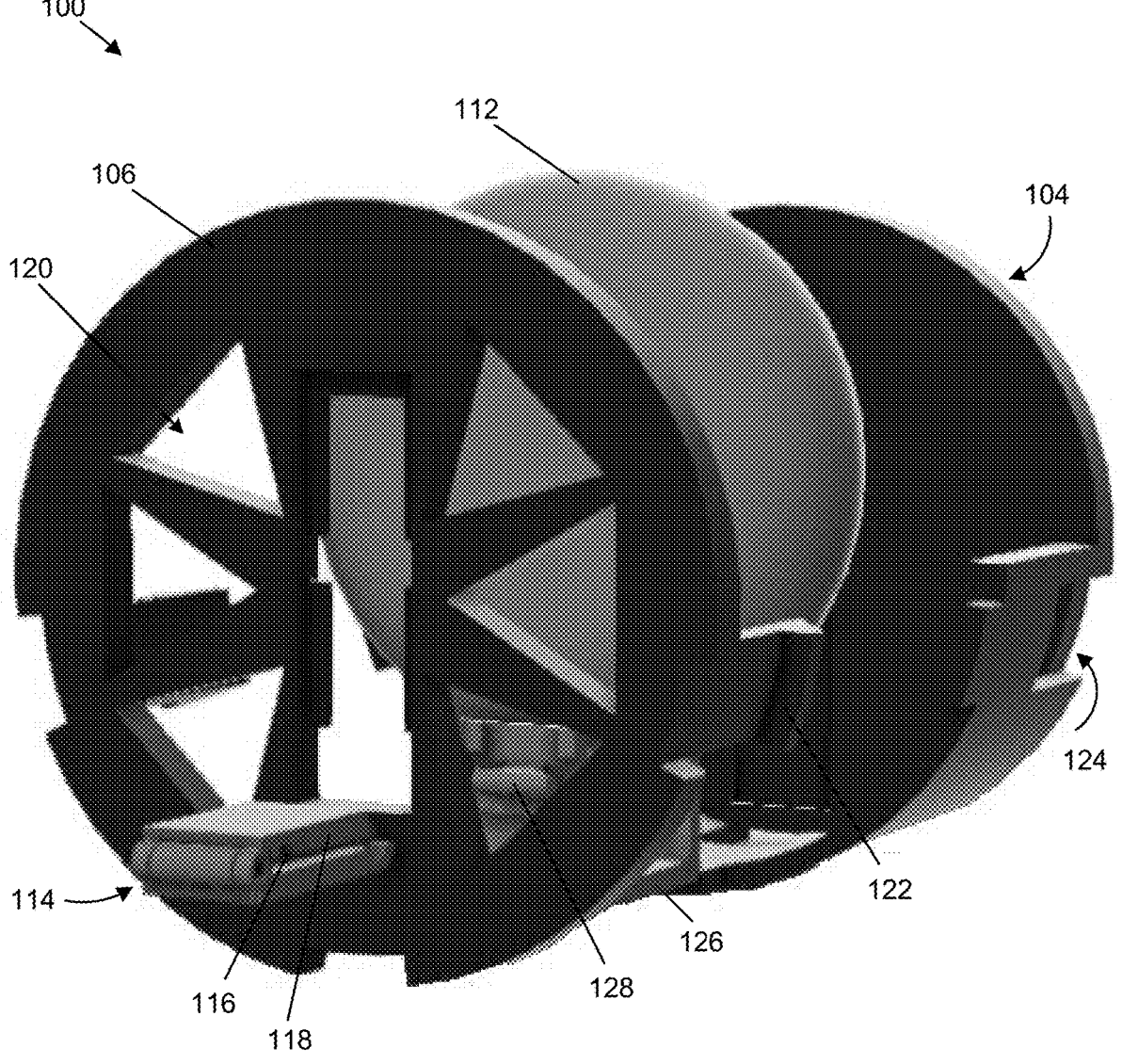
FIG. 1G illustrates another exploded view of an embodi-ment of an air freshener holder in accordance with the subject matter disclosed herein.

FIG. 1G illustrates another exploded view of an embodiment of an air freshener holder 100.

Figure 1H:
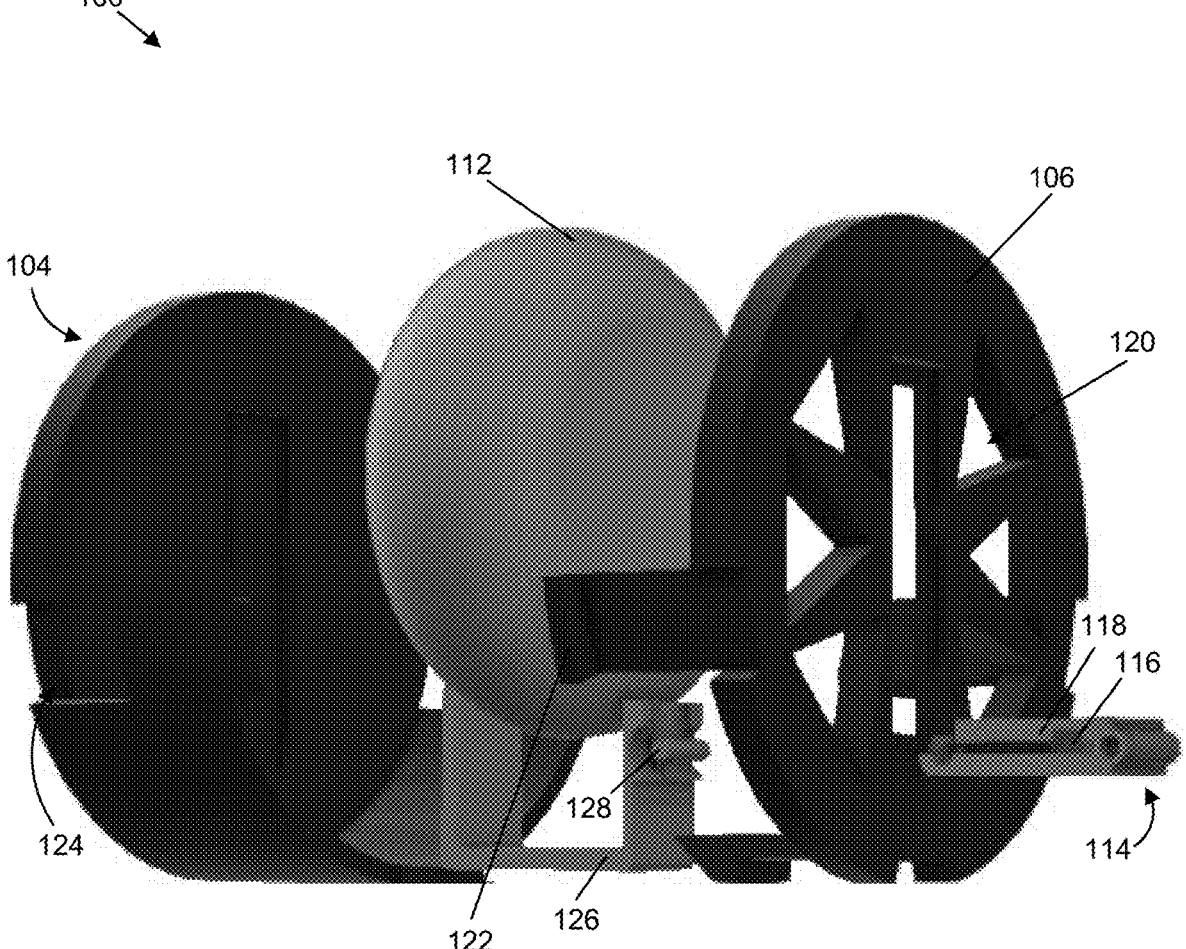
FIG. 1H illustrates another exploded view of an embodi-ment of an air freshener holder in accordance with the subject matter disclosed herein.

FIG. 1H illustrates another exploded view of an embodiment of an air freshener holder 100.

Figure 2:
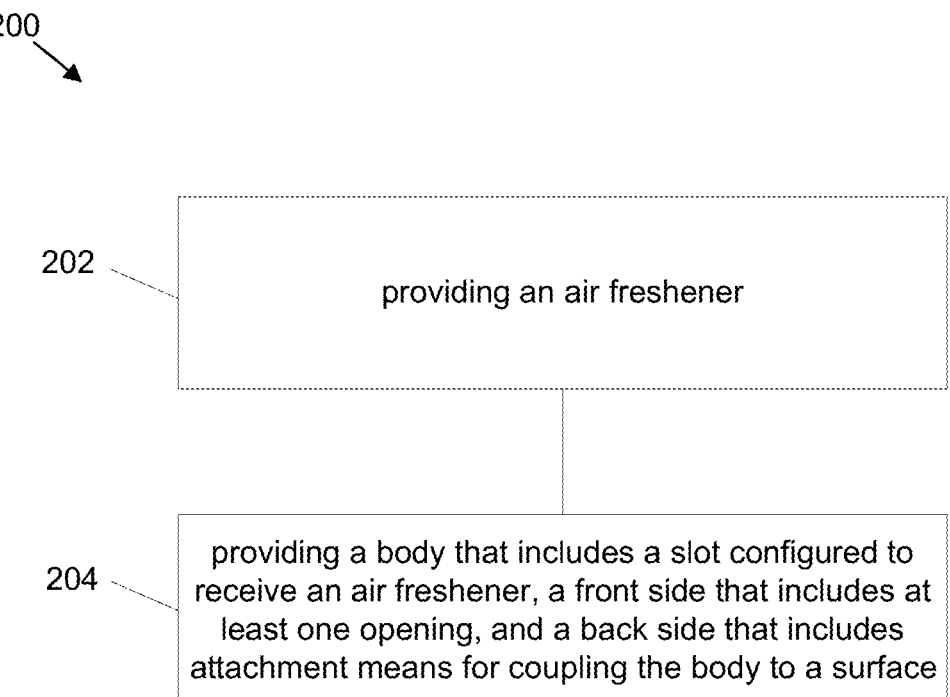
FIG. 2 illustrates an embodiment of a method in accor-dance with the subject matter disclosed herein.

FIG. 2 depicts one embodiment of a method 200 for an air freshener holder. In one embodiment, the method 200 begins and provides 202 an air freshener. In one embodiment, the method 200 provides 204 a body that includes a slot configured to receive an air freshener, a front side that includes at least one opening, and a back side that includes attachment means for coupling the body to a surface, and the method 200 ends.

In one embodiment, an apparatus includes a body that includes a slot configured to receive an air freshener, a front side that includes at least one opening, and a back side that includes attachment means for coupling the body to a surface.

In one embodiment, the body has a substantially cylindrical shape. In one embodiment, the slot has a round shape for receiving air fresheners with corresponding round shapes.

In one embodiment, the apparatus includes an external holder on the front side for attaching a different air freshener to the air freshener holder. In one embodiment, the external holder includes a groove for receiving an attachment member of the different air freshener. In one embodiment, the groove is located between a lever mechanism that is opened to allow insertion of the attachment member of the different air freshener and closed to secure the attachment member to the body. In one embodiment, the lever mechanism is locked in a closed position using securing means.

In one embodiment, the external holder is coupled to the body using a hinge such that the external holder can be folded into a recess of the body. In one embodiment, the apparatus includes securing means for securing the external holder within the recess of the body. In one embodiment, the securing means comprises a push lock mechanism. In one embodiment, the back side is flexible to conform to surfaces of various contours, shapes, textures, or a combination thereof.

In one embodiment, a system includes an air freshener and a body that includes a slot configured to receive an air freshener, a front side that includes at least one opening, and a back side that includes attachment means for coupling the body to a surface.

In one embodiment, the body has a substantially cylindrical shape. In one embodiment, the slot has a round shape for receiving air fresheners with corresponding round shapes.

In one embodiment, the system includes an external holder on the front side for attaching a different air freshener to the air freshener holder. In one embodiment, the external holder includes a groove for receiving an attachment member of the different air freshener. In one embodiment, the groove is located between a lever mechanism that is opened to allow insertion of the attachment member of the different air freshener and closed to secure the attachment member to the body. In one embodiment, the lever mechanism is locked in a closed position using securing means.

In one embodiment, the external holder is coupled to the body using a hinge such that the external holder can be folded into a recess of the body. In one embodiment, the system includes securing means for securing the external holder within the recess of the body. In one embodiment, the securing means comprises a push lock mechanism. In one embodiment, the back side is flexible to conform to surfaces of various contours, shapes, textures, or a combination thereof.

In one embodiment, a method includes providing an air freshener and providing a body that includes a slot configured to receive an air freshener, a front side that includes at least one opening, and a back side that includes attachment means for coupling the body to a surface.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
a body comprising:
a slot configured to receive an air freshener;
a front side comprising at least one opening;
a back side comprising attachment means for coupling the body to a surface; and
an external holder on the front side for attaching a different air freshener to the apparatus, wherein the external holder is coupled to the body using a hinge such that the external holder can be folded into a recess of the body.

2. The apparatus of claim 1, wherein the body has a substantially cylindrical shape.

3. The apparatus of claim 1, wherein the slot has a round shape for receiving the air freshener with a corresponding round shape.

4. The apparatus of claim 1, wherein the external holder includes a groove for receiving an attachment member of the different air freshener.

5. The apparatus of claim 4, wherein the groove is located between a lever mechanism that is opened to allow insertion of the attachment member of the different air freshener and closed to secure the attachment member to the body.

6. The apparatus of claim 5, wherein the lever mechanism is locked in a closed position using securing means.

7. The apparatus of claim 1, further comprising securing means for securing the external holder within the recess of the body.

8. The apparatus of claim 7, wherein the securing means comprises a push lock mechanism.

9. The apparatus of claim 1, wherein the back side is flexible to conform to surfaces of various contours, shapes, textures, or a combination thereof.

10. A system, comprising:
an air freshener; and
a body comprising:
a slot configured to receive the air freshener;
a front side comprising at least one opening;
a back side comprising attachment means for coupling the body to a surface; and
an external holder on the front side for attaching a different air freshener to the body, wherein the external holder is coupled to the body using a hinge such that the external holder can be folded into a recess of the body.

11. The system of claim 10, wherein the air freshener has a round shape that corresponds to a shape of the slot.

12. The system of claim 10, wherein the external holder includes a groove for receiving an attachment member of the different air freshener.

13. The system of claim 12, wherein the groove is located between a lever mechanism that is opened to allow insertion of the attachment member of the different air freshener and closed to secure the attachment member to the body.

14. The system of claim 13, wherein the lever mechanism is locked in a closed position using securing means.

15. The system of claim 10, further comprising securing means for securing the external holder within the recess of the body, the securing means comprises a push lock mechanism.

16. A method, comprising:

providing an air freshener; and providing a body comprising:

a slot configured to receive the air freshener;

a front side comprising at least one opening;     5 a back side comprising attachment means for coupling the body to a surface; and an external holder on the front side for attaching a different air freshener to the body, wherein the external holder is coupled to the body using a hinge such 10 that the external holder can be folded into a recess of the body.

\* \* \* \* \*